(12) United States Patent
McDowall

(10) Patent No.: US 8,437,629 B2
(45) Date of Patent: May 7, 2013

(54) DUAL OPTICAL PATH PRISM AND CAMERA IN A MINIMALLY INVASIVE SURGICAL SYSTEM

(71) Applicant: Ian E. McDowall, Woodside, CA (US)

(72) Inventor: Ian E. McDowall, Woodside, CA (US)

(73) Assignee: Intuitive Surgical Operations, Inc, Sunnyvale, CA (US)

( * ) Notice: Subject to any disclaimer, the term of this patent is extended or adjusted under 35 U.S.C. 154(b) by 0 days.

(21) Appl. No.: 13/633,729

(22) Filed: Oct. 2, 2012

(65) Prior Publication Data

US 2013/0027533 A1    Jan. 31, 2013

Related U.S. Application Data

(63) Continuation of application No. 12/855,934, filed on Aug. 13, 2010, now Pat. No. 8,295, 693.

(60) Provisional application No. 61/361,272, filed on Jul. 2, 2010.

(51) Int. Cl.
*A61B 1/04* (2006.01)

(52) U.S. Cl.
USPC ............................................. 396/17; 359/722

(58) Field of Classification Search .................. 359/722; 396/17
See application file for complete search history.

(56) References Cited

U.S. PATENT DOCUMENTS

| | | | |
|---|---|---|---|
| 4,074,306 A | 2/1978 | Kakinuma et al. | |
| 4,473,841 A | 9/1984 | Murakoshi et al. | |
| 6,331,181 B1 | 12/2001 | Tierney et al. | |
| 6,720,988 B1 | 4/2004 | Gere et al. | |
| 8,295,693 B2 | 10/2012 | McDowall | |
| 2004/0145814 A1* | 7/2004 | Rogers | 359/634 |
| 2006/0067662 A1* | 3/2006 | Satori | 396/72 |
| 2006/0092273 A1 | 5/2006 | Gere et al. | |
| 2008/0065105 A1 | 3/2008 | Larkin et al. | |
| 2009/0268010 A1 | 10/2009 | Zhao et al. | |
| 2011/0082369 A1 | 4/2011 | Mohr et al. | |
| 2011/0249323 A1* | 10/2011 | Tesar et al. | 359/356 |
| 2012/0002956 A1 | 1/2012 | McDowall | |

FOREIGN PATENT DOCUMENTS

WO    2010042522 A1    4/2010

OTHER PUBLICATIONS

PCT/US2011/041468 International Search Report and Written Opinion of the International Searching Authority, mailed Sep. 23, 2011, 10 pages.

RPC Photonics, "Diffractive Optical Elements", Jun. 2008, http://web.archive.org/web/20080622095236/http://www.rpcphotonics.com/opt-ical.asp.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

*Primary Examiner* — Clayton E Laballe
*Assistant Examiner* — Dennis Hancock

(57) ABSTRACT

In a minimally invasive surgical system, a camera includes a prismatic element having a lens within the prismatic element. The lens corrects the resulting image focus for the non-visible light to make it substantially the same as the focus for the visible light. Alternatively, the lens corrects the resulting image focus for the visible light to make it substantially the same as the focus for the non-visible light.

18 Claims, 10 Drawing Sheets

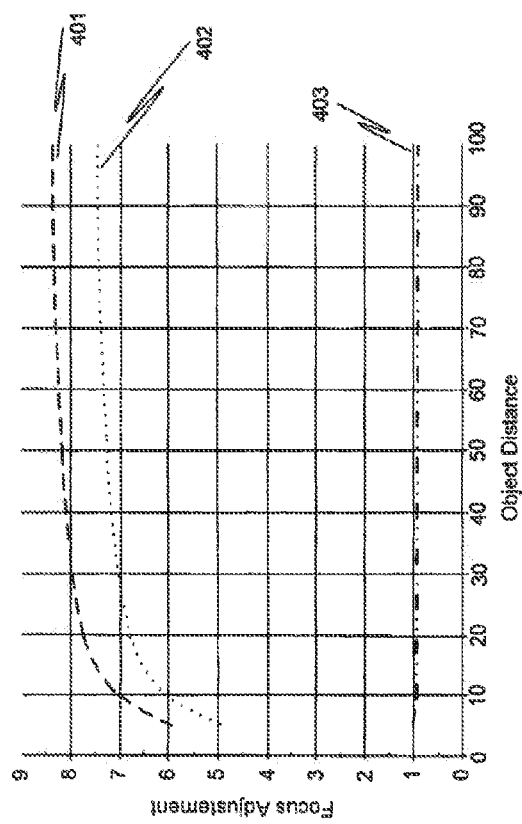
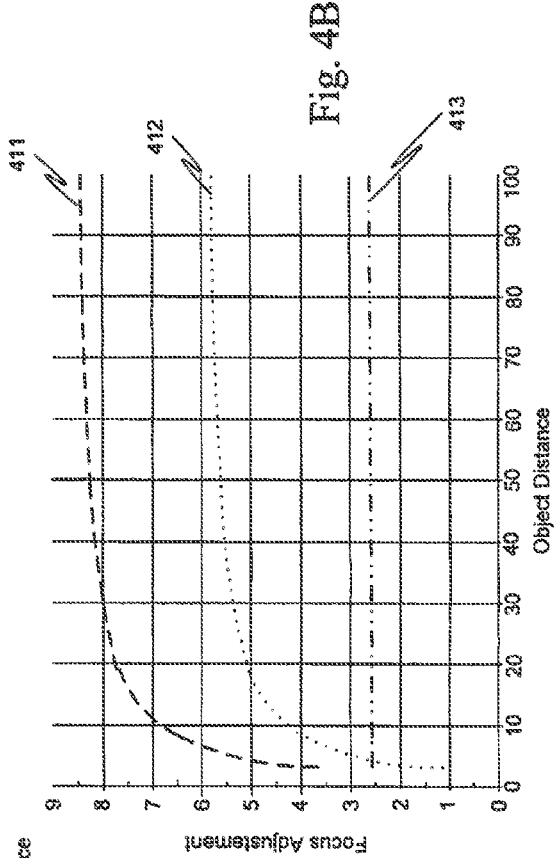
Fig. 4A
Fig. 4B

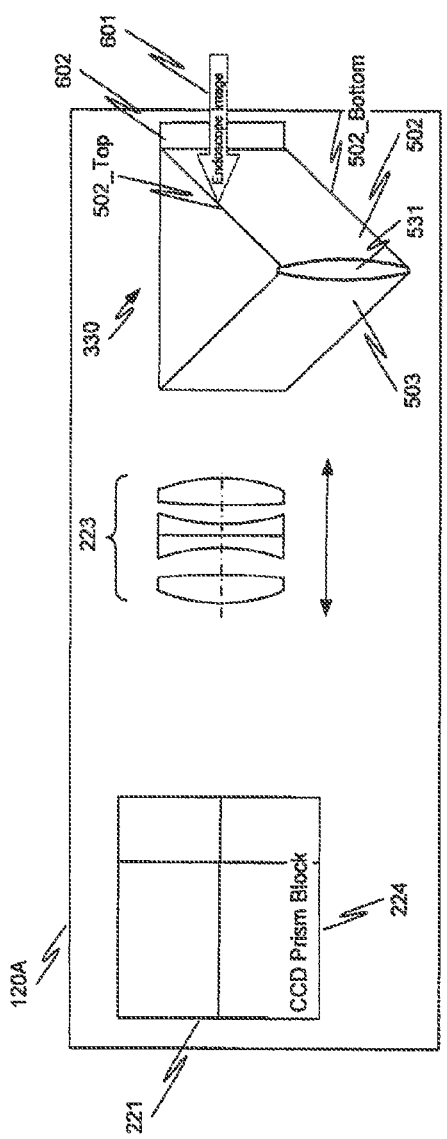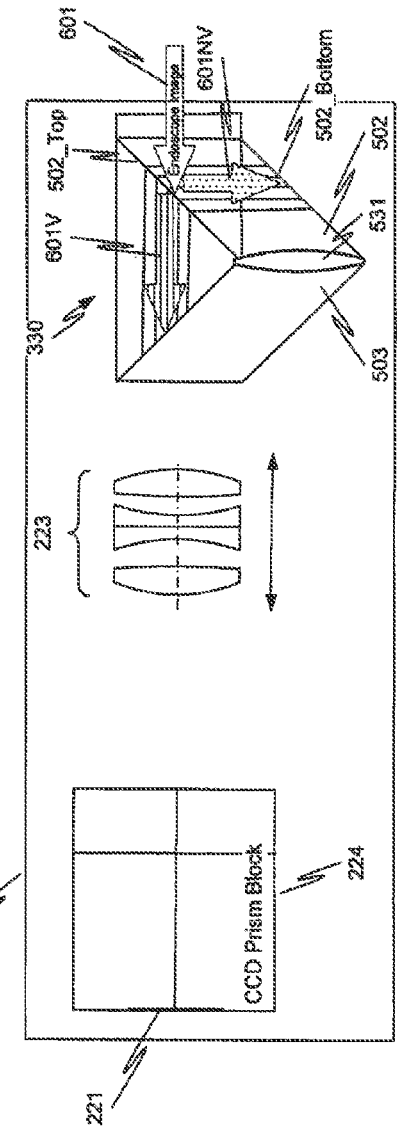

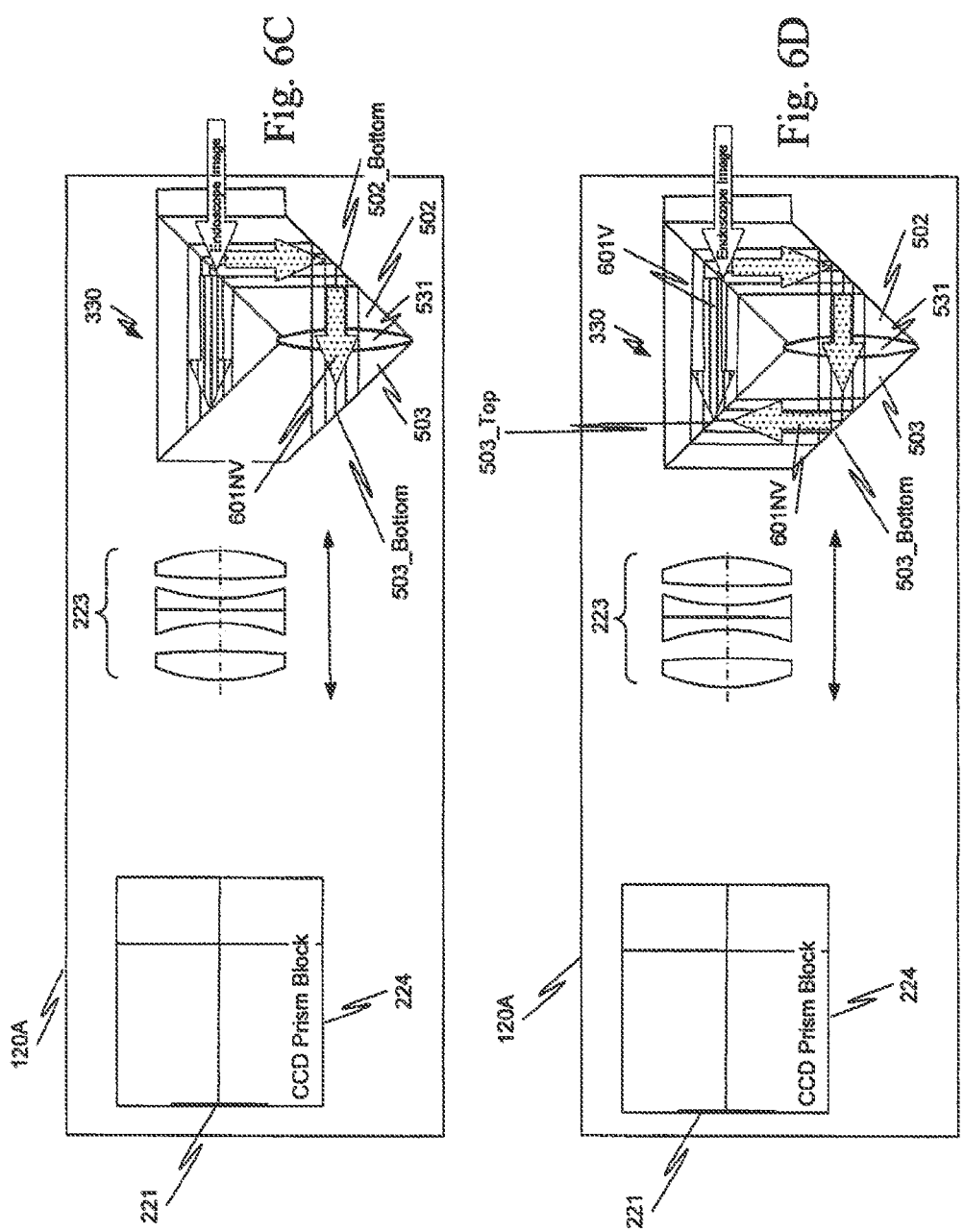

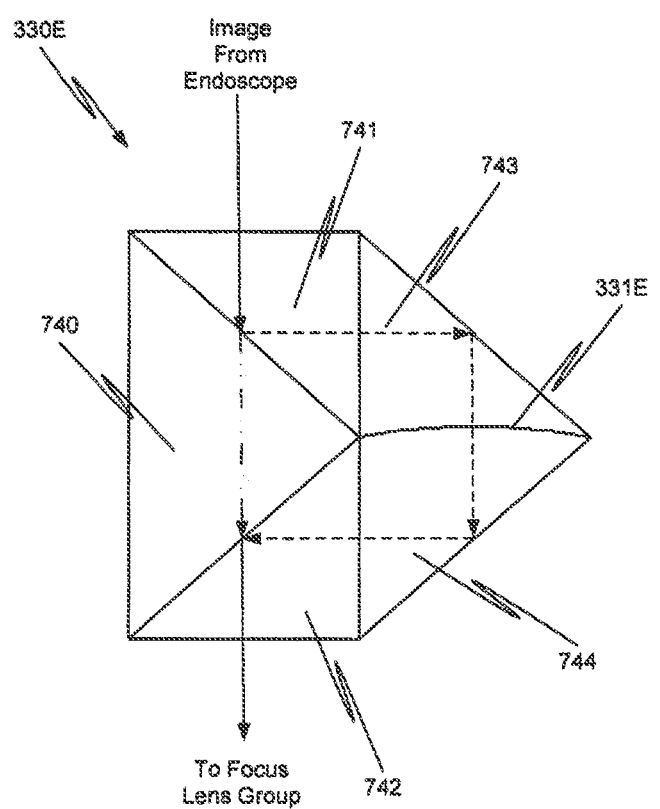

DUAL OPTICAL PATH PRISM AND CAMERA IN A MINIMALLY INVASIVE SURGICAL SYSTEM

RELATED APPLICATION

This application is a continuation of U.S. patent application No. 12/855,934 (filed Aug. 13, 2010, now U.S. Pat. No. 8,295,693), which claims priority to and the benefit of U.S. patent application No. 61/361,272 (filed Jul. 2, 2010), which is incorporated herein by reference in its entirety.

BACKGROUND

1. Field of Invention

Aspects of this invention are related to endoscopic imaging and are more particularly related to simultaneously focusing visible light images and near infrared or ultraviolet images.

2. Related Art

The da Vinci® Surgical System, commercialized by Intuitive Surgical, Inc., Sunnyvale, Calif., is a minimally invasive teleoperated surgical system that offers patients many benefits, such as reduced trauma to the body, faster recovery and shorter hospital stay. One key component of the da Vinci® Surgical System is a capability to provide two-channel (i.e., left and right) video capture and display of visible images to provide stereoscopic viewing for the surgeon.

Such electronic stereoscopic imaging systems may output high definition video images to the surgeon, and may allow features such as zoom to provide a "magnified" view that allows the surgeon to identify specific tissue types and characteristics, as well as to work with increased precision. In a typical surgical field, however, certain tissue types are difficult to identify, or tissue of interest may be at least partially obscured by other tissue. This complicates the surgical procedure.

In some applications, fluorescence images in the near infrared spectrum and reflected white light images are used in minimally invasive surgery. But, the back focal distance for a near infrared fluorescence image is different from the back focal distance for a reflected white light image. Thus, when switching from one mode of operation or the other a focus adjustment is required. When both a near infrared fluorescence image and a reflected white light image are being viewed simultaneously, the typical optics in an endoscope and camera do not provide simultaneous focus of both images. A similar situation may also occur in the ultraviolet spectrum.

One solution to the differences in focal plane for different wavelength images is presented in International Publication Number WO 2010/042522A1 published 15 Apr. 2010. This approach utilizes a prism including sections made of different materials having different indices of refraction. A dichroic coating is placed on the diagonal surface between the sections so that one half of the diagonal surface is coated with a short pass coating that transmits visible light and reflects near infrared light. The other half of the diagonal surface is coated with a long pass coating that transmits near infrared light and reflects visible light.

This approach works for small differences in focus. However, this approach is not practical for larger differences in focus because the size of the prism required becomes too great. This approach also requires a physically larger camera as the imaging path becomes offset laterally by some amount resulting in a larger camera assembly. This approach also requires finding two materials with exactly the "correct" indexes and Abbe numbers to satisfy the design. There are a limited number of suitable materials so a solution may not be possible. This approach also cannot correct more general optical aberrations.

SUMMARY

In one aspect, an endoscopic camera properly focuses both visible and non-visible images after being configured to focus one of the images. The camera, in one aspect, includes a prismatic element having a lens within the prismatic element. The lens corrects for the longitudinal (axial) color created by the endoscope optics at the wavelength range of interest in the near infrared so that the visible image and the near infrared image both come to a focus at the imaging sensor in the camera. An image capture device and focusing optics within the camera may be maintained unchanged.

The term fluorescence used here is emitted light in the near infrared spectrum, but this is illustrative only and is not intended be limiting. In view of this disclosure, fluorescence can be processed that is emitted light either in the near infrared spectrum or in the ultraviolet spectrum.

Near infrared imaging through optics not intentionally designed to have good performance in the near infrared likely exhibit both axial color aberration and other optical aberrations. The lens in the prismatic element may also mitigate some of the other aberrations.

In one aspect, the lens in the prismatic element is changeable so that the camera can be used with endoscopes having different optical characteristics. In another aspect, the lens is formed in faces of two adjacent prisms in the prismatic element. Alternatively, the curved surfaces can be on the hypotenuse surfaces of the prisms in the alternate path. In yet another aspect, a diffractive element is used in place of the lens.

In another aspect, the non-visible light is fluorescence and the visible light includes a visible component of white light in one example. In still yet another aspect, the fluorescence is near infrared fluorescence.

A method includes receiving, from a minimally invasive surgical instrument, light including visible light and non-visible light. The visible light is separated from the non-visible light.

In this method, one of the visible light and the non-visible light is passed through a lens. The lens corrects a focus of the image formed from one of the visible light and the non-visible light so that the overall system focal length (measured at the wavelength being imaged) of the optics creating the visible and non-visible images is about the same, resulting in reasonable focus of the images formed from the visible light and non-visible light.

Also, in this method the one of the visible light and the non-visible light from the lens is recombined with the other of the visible light and the non-visible light. The recombined visible light and non-visible light are focused.

In another aspect of the method, one of the visible light and the non-visible light is passed through a lens. The lens corrects a focus of an image formed from one of the visible light and the non-visible light so that the focus of the image is about the same as a focus of an image formed from the other of the visible light and non-visible light. The one of the visible light and the non-visible light from the lens is recombined with the other of the visible light and the non-visible light.

In yet another aspect of the method, one of the visible light and the non-visible light is passed through a lens. The lens modifies aberrations of an image formed from one of the visible light and the non-visible light so that a perceived focus of the image is about the same as a focus of an image formed from the other of the visible light and non-visible light. The one of the visible light and the non-visible light from the lens is recombined with the other of the visible light and the non-visible light.

A minimally invasive surgical system includes a camera including a prismatic element having a lens within the prismatic element. In one aspect, a diffractive element is used in place of the lens. The lens corrects the focus of an image formed from the one of the visible light and the non-visible light so that the focus of the image is about the same as a focus of another image formed from an other of the visible light and non-visible light that passes through the prismatic element.

The prismatic element includes a first surface having a pass, reflect coating. The coating passes the other of the visible light and the non-visible light through the coating, and reflects the one of the visible light and the non-visible light.

The prismatic element also include a second surface, opposite and removed from the first surface, having a reflect coating.

The prismatic element includes a plurality of prisms. In one aspect, the lens is formed in faces of two adjacent prisms in the plurality of prisms.

In yet another aspect, a minimally invasive surgical system includes a camera having an imaging plane, and a focus correction assembly. The focus correction assembly includes a first optical path, a second optical path comprising a lens, a common start location, and a common end location. The length of the second optical path is longer than the length of the first optical path.

The focus correction assembly is configured and positioned with reference to the camera so that light in a first spectrum that passes from the start location through the first optical path to the end location and light in a second spectrum that passes from the start location through the second optical path to the end location are both focused on the imaging plane to form a visible image and an non-visible image that are substantially in focus on the imaging plane.

BRIEF DESCRIPTION OF THE DRAWINGS

FIG. 4A is a graph of the focus characteristics of visible and non-visible images from a first endoscope.

FIG. 4B is a graph of the focus characteristics of visible and non-visible images from a second endoscope.

FIGS. 6A to 6E illustrate the operation of the prismatic element of FIG. 5.

FIGS. 7A to 7E illustrative alternative implementations of the prismatic element.

Figure 1:
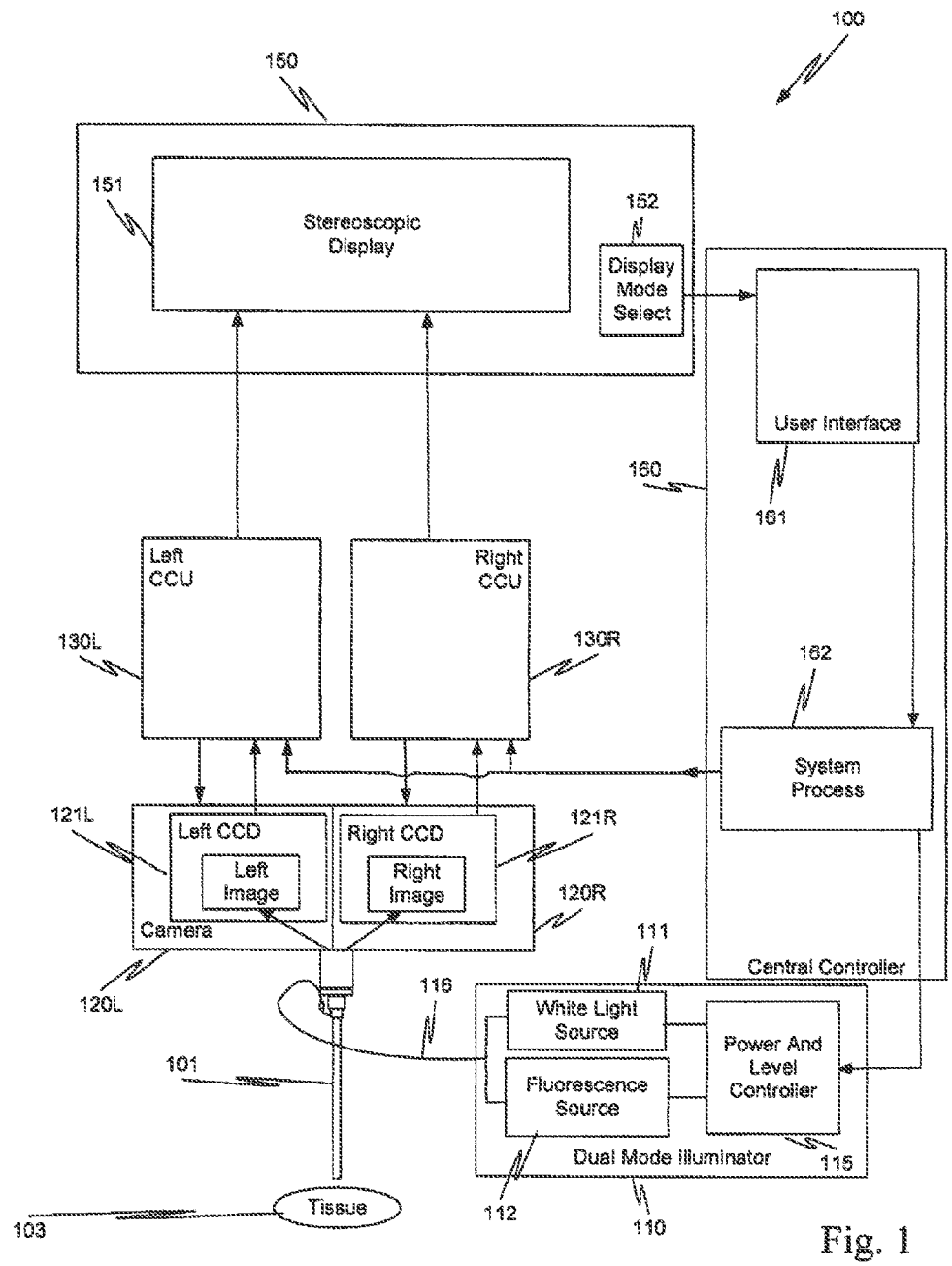
FIG. 1 is a high-level diagrammatic view of a minimally invasive teleoperated surgical system that includes an endoscopic camera with a common focus for visible and non-visible images.

In the drawings, the first digit of a reference number indicates the figure in which the element with that reference number first appeared.

DETAILED DESCRIPTION

As used herein, electronic stereoscopic imaging includes the use of two imaging channels (i.e., channels for left and right images).

As used herein, a stereoscopic optical path includes two channels in an endoscope for transporting light from tissue (e.g., channels for left and right images). The light transported in each channel represents a different view of the tissue. The light can form one or more images. Without loss of generality or applicability, the aspects described more completely below also could be used in the context of a field sequential stereo acquisition system and/or a field sequential display system.

As used herein, an illumination path includes a path in an endoscope providing illumination to tissue.

As used herein, images captured in the visible electromagnetic radiation spectrum are referred to as acquired visible images.

As used herein, white light is visible white light that is made up of three (or more) visible color components, e.g., a red visible color component, a green visible color component, and a blue visible color component. If the visible color components are provided by an illuminator, the visible color components are referred to as visible color illumination components. White light may, also refer to a more continuous spectrum in the visible spectrum as one might see from a heated tungsten filament, for example.

As used herein, a visible image includes a visible color component.

As used herein, a non-visible image is an image that does not include any of the three visible color components; thus, a non-visible image is an image formed by light outside the range typically considered visible.

As used herein, images captured in the visible electromagnetic radiation spectrum are referred to as acquired visible images.

As used herein, images captured as the result of fluorescence are referred to herein as acquired fluorescence images. There are various fluorescence imaging modalities. Fluorescence may result from the use of, for example, injectable dyes, fluorescent proteins, or fluorescent tagged antibodies, Fluorescence may result from, for example, excitation by laser or other energy source. Fluorescence images can provide vital in vivo patient information that is critical for surgery, such as pathology information (e.g., fluorescing tumors) or anatomic information (e.g., fluorescing tagged tendons). In the following description, fluorescence in the near infrared spectrum is used as an example.

As used herein a pass, reflect coating is a coating that passes wavelengths with a first predefined relationship to a transition wavelength and reflects wavelengths with a second predefined relationship to the transition wavelength. For example, as used herein a short pass, long reflect coating is a coating that predominately passes wavelengths shorter than a transition wavelength and predominately reflects wavelengths longer than the transition wavelength. Thus, in this example, the first predefined relationship is shorter than, and the second predefined relationship is longer than.

Aspects of this invention facilitate acquiring, in focus, visible and non-visible images from a surgical field by cameras 120L, 120R (FIG. 1) in a minimally invasive surgical system 100, e.g., the da Vinci® minimally invasive teleoperated surgical system commercialized by Intuitive Surgical, Inc. of Sunnyvale, Calif. In one aspect, cameras 120L, 120R are used in a minimally invasive surgical system that includes two viewing modes: a normal mode and one or more augmented modes. A person switches between the viewing modes using display mode switch 152 that typically is on a surgeon's console 150.

In the normal viewing mode, visible images of the surgical field are acquired by cameras 120L, 120R and displayed in stereoscopic display 151. In the augmented mode, non-visible images are acquired by cameras 120L, 120R. The acquired non-visible images are processed, e.g., false colored using a visible color component, and presented in stereoscopic display 151. In some aspects, the augmented mode may also acquire visible images.

Cameras 120L, 120R properly focus both visual images and non-visible images on capture components 121L, 121R, respectively without making any focus adjustments to the cameras when the different images are acquired. In one aspect, cameras 120L, 120R are focused to acquire the visual images with capture components 121L, 121R, and the non-visible images are acquired in focus with the same capture components 121L, 121R without any further adjustments to cameras 120L, 102R.

As explained more completely below, each of cameras 120L, 120R includes a prismatic element with a lens (or other device with optical power such as a binary surface or material with varying refractive index) within the prismatic element. For example, in one aspect, a diffractive element is used in place the lens. The diffractive element has a diffractive optical surface comprised of small structures which afford the ability to modify the wavefront. The diffractive surface could be fabricated by a number of techniques including holography, or by creating a kinoform or binary surface. In a prismatic element with a diffractive surface, the light path through the diffractive element can have a relatively restricted wavelength range which facilitates the implementation of such a surface.

In one aspect, non-visible light, which can form the non-visible image, is passed through the lens. The lens corrects the focus of the non-visible image so that the focus of the non-visible images is about the same as a focus of the visible image.

The prismatic element has no noticeable effect on the visible images. Cameras 120L, 120R require no changes to the optical prescription in endoscope 101 while providing a solution to the different image positions, sometimes called planes, formed by the optics for the visible and non-visible images.

Prior to considering cameras 120L, 120R in further detail, minimally invasive surgical system 100 is described. System 100 is illustrative only and is not intended to limit the application of cameras 120L, 1200 to this specific system.

Minimally invasive surgical system 100, for example, the da Vinci® Surgical System, includes cameras 120L, 120R. In this example, a surgeon at surgeon's console 150 remotely manipulates an endoscope 101 mounted on a robotic manipulator arm (not shown). There are other parts, cables, etc. associated with the da Vinci® Surgical System, but these are not illustrated in FIG. 1 to avoid detracting from the disclosure. Further information regarding minimally invasive surgical systems may be found for example in U.S. patent application Ser. No. 11/762,165 (filed Jun. 13, 2007; disclosing Minimally Invasive Surgical System) and U.S. Pat. No. 6,331,181 (filed Dec. 18, 2001; disclosing Surgical Robotic Tools, Data Architecture, and Use), both of which are incorporated herein by reference.

An illumination system, e.g., dual mode illuminator 110, is coupled to endoscope 101. Dual mode illuminator 110 includes a white light source 111 and a fluorescence excitation source 112. The particular implementation of sources 111 and 112 is not critical. Dual mode illuminator 110 is used in conjunction with at least one illumination path in stereoscopic endoscope 101 to illuminate tissue 103.

In one example, dual mode illuminator 110 has two modes of operation: a normal display mode and an augmented display mode. In the normal display mode, white light source 111 provides illumination that illuminates tissue 103 in white light. Fluorescence excitation source 112 is not used in the normal display mode.

In the augmented display mode, white light source 111 provides, in one aspect, one or more visible color components to illuminate tissue 103. In another aspect, none of the visible color components of white light are used when fluorescence excitation source 112 is on. Typically, three (or more) visible color components make up white light, i.e., white light includes a first visible color component, a second visible color component, and a third visible color component. Each of the three visible color components is a different visible color component, e.g., a red component, a green component, and a blue component. More color components may also be used such as cyan.

In the augmented display mode, fluorescence excitation source 112 provides a fluorescence excitation illumination component that excites fluorescence images of tissue 103. For example, narrow band light from fluorescence excitation source 112 is used to excite tissue-specific near infrared emitting fluorophores so that fluorescence images of specific tissue within tissue 103 are acquired by cameras 120L, 120R.

In one aspect, white light source 111 includes a source for each of the different visible color illumination components. For a red-green-blue implementation, in one example, the sources are lasers—a red laser, a green laser and a blue laser. Table 1 gives the range of output wavelengths for each of the lasers used in this example.

TABLE 1

| Visible Color Illumination Component | Wavelength |
| --- | --- |
| Red | 670 nanometers (nm) |
| Green | 550 nm |
| Blue | 450 nm |

The use of lasers in white light source 111 is illustrative only and is not intended to be limiting. White light source 111 could also be implemented with multiple laser diode sources, or light emitting diodes instead of lasers for example, and could employ more than the three dominant wavelength peaks in the visible spectrum. Alternatively, white light source 111 could use a Xenon lamp with an elliptic back reflector and a band pass filter coating to create broadband white illumination light for visible images. The use of a Xenon lamp also is illustrative only and is not intended to be limiting. For example, a high pressure mercury arc lamp, other arc lamps, or other broadband light sources may be used.

When the fluorescence excitation wavelength occurs outside the visible spectrum (e.g., in the near infrared (NIR) spectrum), a laser module (or other energy source, such as a light-emitting diode or filtered white light) is used as fluorescence excitation source 112.

Thus, in one aspect, fluorescence is triggered by light from a laser module in fluorescence excitation source 112. As an example, fluorescence was excited using an 808 nm laser, and the fluorescence emission maximum was at 835 nm.

In either the normal or augmented display modes, the light from the light source or light sources is directed into a fiber optic bundle 116. Fiber optic bundle 116 provides the light to an illumination path in stereoscopic endoscope 101 that in turn directs the light to tissue 103.

Endoscope 101 also includes, in one aspect, two optical channels for passing light from tissue 103, e.g., reflected white light and/or fluorescence. The reflected white light is a normal visible image or images.

The light from tissue 103 (FIG. 1) is passed by the stereoscopic optical path in endoscope 101 to cameras 120L, 120B. As explained more completely below, camera 120L includes a prismatic element, a focus lens group, and in this aspect, a left image charge coupled device (CCD) 121L. Similarly, camera 120B includes a prismatic element, a focus lens group, and in this aspect, a right image CCD 121R.

In the various modes of operation, left image CCD 121L acquires a left image and right image CCD 121R acquires a right image. Each of left image CCD 121L and right image CCD 121R can be multiple CCDs that each capture a different visible color component; a single CCD with different regions of the CCD that capture a particular visible color component, etc. A three-chip CCD sensor is illustrative only. A single CMOS image sensor with a color filter array or a three-CMOS color image sensor assembly may also be used.

Camera 120L is coupled to a stereoscopic display 151 in surgeon's console 150 by a left camera control unit 130L. Camera 120R is coupled to stereoscopic display 151 in surgeon's console 150 by a right camera control unit 130R. Camera control units 130L, 130B receive signals from a system process 162. System process 162 represents the various controllers in system 100.

Display mode select switch 152 provides a signal to a user interface 161 that in turn passes the selected display mode to system process 162. Various controllers within system process 162 configure the power and level controller 115 within dual mode illuminator 110, configure left and right camera control units 130L and 130R to acquire the desired images, and configure any other elements needed to process the acquired images so that the surgeon is presented the requested images in display 150.

The particular technique used to combine the acquired visible images and fluorescence images for display is not essential to understanding the novel approach for correcting the differences in focus between visible and non-visible images. Irrespective of the viewing mode, visible only, fluorescence only, or combined visible and fluorescence, both the acquired images and the displayed images remain generally in focus without any adjustment to the system after the focus is set for the visible images, i.e., without changes to the endoscope optics, without changing the focus of the cameras and without any processing of the acquired images to compensate for differences in focus between the acquired visible and fluorescence images.

Figure 2:
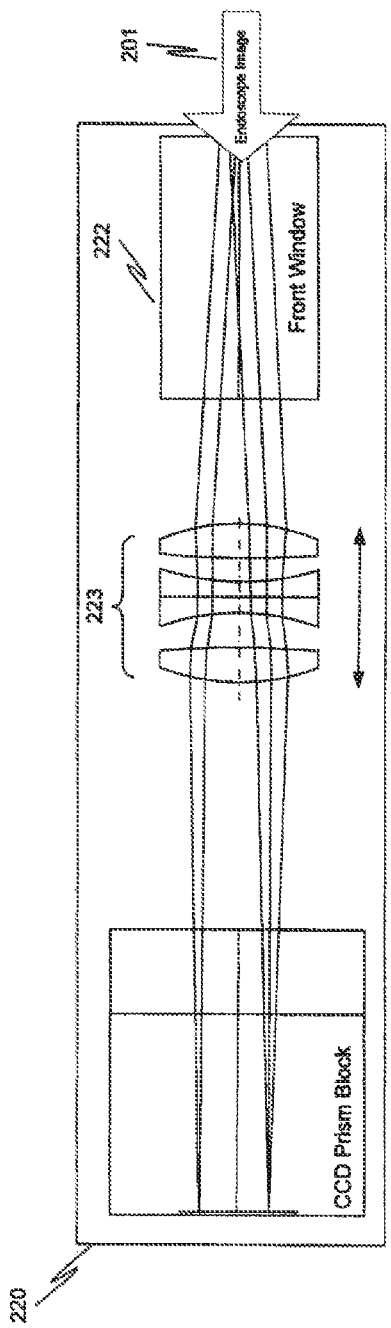
FIG. 2 is a block diagram of a prior art endoscopic camera.

FIG. 2 is a block diagram of a prior art camera 220 used with each image channel of endoscope 101. An endoscope image 201 is an image of tissue 103 from endoscope 101. Image 201 passes through a front window 222 to a focus lens group 223, which is an example of a focus unit.

Focus lens group 223 moves along a longitudinal axis of camera 220. Focus lens group 223 is positioned so that image 201 is focused on COD 221 in COD prism block 224. Unfortunately, as noted above, the focus is different for visible images and non-visible images.

If image 210 is a visible image, focus lens group 223 is positioned at a first location to focus the visible component(s) on COD 221. If image 210 is a non-visible image, e.g., in the near infrared spectrum, which typically includes wavelengths in the range of 700 nm to 1000 nm, focus lens group 223 is positioned at a second location to focus the non-visible image on CCD 221. The first and second locations are different. This difference in focus is particularly noticeable when going from capturing a fluorescence image to a visible image or vice versa.

Figure 3:
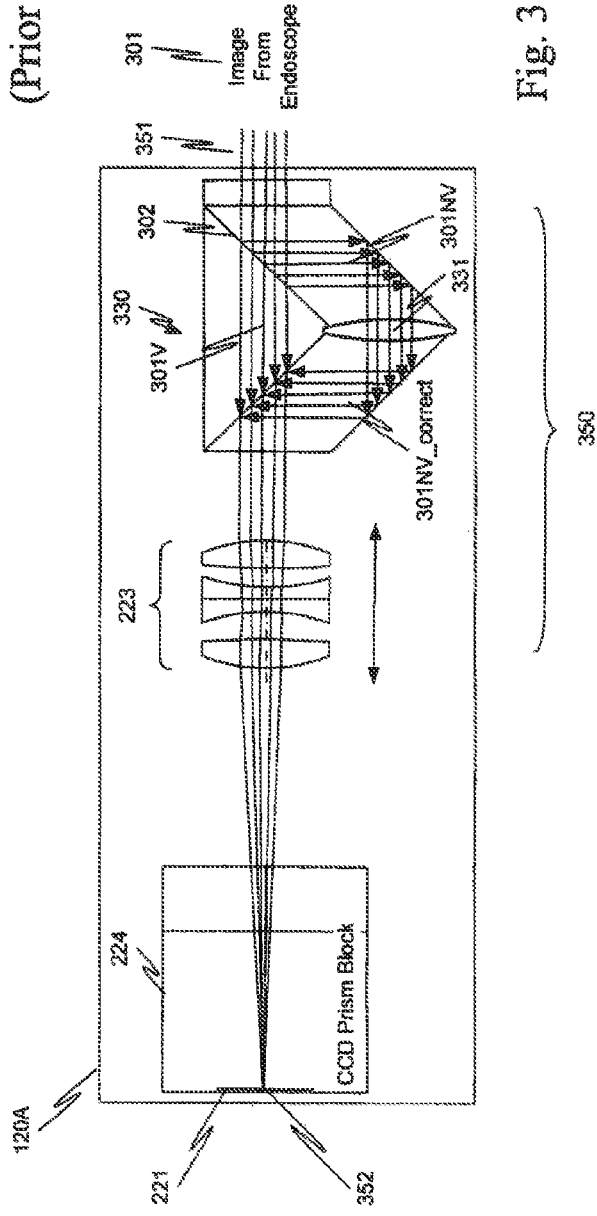
FIG. 3 is a block diagram of a novel camera that includes a prismatic element with a lens, a focus lens group, a CCD prism block, and a CCD.

FIG. 3 is a block diagram of novel focus correction assembly used with each channel of endoscope 101. In this example, the novel focus correction assembly is included in camera 120A. Camera 120A can be used as camera 120L and as camera 120R. Also, the novel focus correction assembly can be used with a monoscopic endoscope. In camera 120A, prior art front window 222 is no longer used and instead a prismatic element 330, sometimes called a prism assembly, is used. Prismatic element 330 includes a lens 331. Focus lens group 223, COD prism block 224 and CCD 221 are the same as in prior art camera 220 and, in one aspect, are used directly in camera 120A, i.e., are unchanged. Focus lens group 223 is a focus unit. CODprism block 224 and COD 221 are an image capture unit.

As explained more completely below, in one aspect, lens 331 corrects the focus of a non-visible light from endoscope 101 so that the focus of the non-visible image formed from the non-visible light is about the same as the focus of a visible image formed from visible light from endoscope 101. Here, "about the same" focus and "substantially" in focus means that when the non-visible image and a visible image are viewed by a person, the difference in focus of the two images is not salient to that person, i.e., the apparent sharpness of the images is similar for both images. In actual fact, the diffraction limited sharpness of the near infrared image is lower than that of the visible as the wavelength is longer. The actual optical system may have other aberrations, which also influence the image sharpness by wavelength.

Also, when it is stated that a person views a non-visible image, it means that the acquired non-visible image has been processed in system 100, e.g., false colored, so that the non-visible image can be presented in display 151 as a visible image. This processing is performed on the image acquired by camera 120A and so does affect the operation of camera 120A as described herein. One example of false coloring is described in copending and commonly filed U.S. patent application Ser. No. 12/575,093 (filed Oct. 7, 2009; disclosing Methods and Apparatus for Displaying Enhanced Imaging Data on a Clinical Image), which is incorporated herein by reference in its entirety.

Above and in the following examples, non-visible light is passed through the lens and the visible light is passed directly through the prismatic element. This is illustrative only and is not intended to be limiting. In view of the disclosure, those knowledgeable in the field can use a lens to focus correct the visible light and pass the non-visible light directly through the prismatic element when such an application is advantageous. Thus, in more general terms, one of visible light and non-visible light is passed through a lens. The other of the visible light and non-visible light is passed directly through the prismatic element.

In the example of FIG. 3, light 301 from the endoscope includes visible light 301V and non-visible light 301NV. Stated in another way, light 301 includes visible wavelengths 301V and non-visible wavelengths 301NV. Visible light 301V is passed directly through prismatic element 330. However, a surface 302 of prismatic element 330, which is an example of a first surface, includes a coating that reflects non-visible light 301NV and allows visible light 301V to pass through. Thus, the coating extracts non-visible light 301NV from light 301, i.e., this results in the separation of visible light 301V, which can form a visible light image, from non-visible light 301NV, which can form a non-visible image.

Extracted non-visible light 301NV is passed through lens 331, which corrects the focus of the image formed by the light 301NV to produce focus-corrected non-visible light 301NV_correct. Focus—corrected non-visible light 301NV_correct is recombined with visible light 301V by prismatic element 330 and the recombined light is passed through focus lens group 223. Now, focus-corrected non-visible light 301NV_correct and visible light 301V have the same virtual position so that focus lens group 223 properly focuses both images on CCD 221

Prismatic element and lens 331 can be formed in a variety of ways as described more completely below. In one aspect, lens 331 is changeable. Thus, a lens can be specified for a particular endoscope and can be inserted in prismatic element 330. If another endoscope requires a different lens, the lenses can be interchanged. Thus, camera 120A can be used with any endoscope so long as an appropriate lens, e.g., a lens that corrects the focus of the non-visible images from the endoscope, is available.

In another aspect, lens 331 is formed in the face of a prism, or in faces of prisms in prismatic element 330. In this aspect, a prismatic element is associated with an endoscope type. For a particular endoscope, the prismatic element that corrects the focus of non-visible images from that endoscope is inserted in camera 120A.

Hence, in one aspect, a minimally invasive surgical system includes an imaging plane, e.g., CCD 221 and a focus correction assembly 350, Focus correction assembly 350 includes a first optical path and a second optical path. The first and second optical paths both extend between a common start location 351 and a common end location 352. The length of the second optical path is longer than the length of the first optical path. The second optical path includes a lens 331. Image focus correction assembly 350 is configured and positioned so that light in a first spectrum that passes from start location 351 through the first optical path to end location 352 and light in a second spectrum that passes from start location 351 through the second optical path to end location 352 are both focused on imaging plane 221 to form images that are substantially in focus on imaging plane 221.

In one aspect, the first optical path is substantially straight and the second optical path is folded. The second optical path includes surface 302 that passes the first spectrum and reflects the second spectrum. In one aspect, described more completely below, the first spectrum includes at least a portion of the visible spectrum and the second spectrum includes a least a portion of the infrared spectrum. In another aspect, the second spectrum is a fluorescence spectrum of a medical fluorophore.

Recall, one prior art solution used materials with different indices of refraction to correct the focus between visible and non-visible images so that different sized structures based on the differences in focal length were required. In contrast, in camera 120A, the size of prismatic element 330 remains unchanged and only the power of the lens within element 330 is changed in one aspect.

FIGS. 4A and 4B are examples of ways to determine an appropriate lens for a particular endoscope. FIG. 4A is for a 12 mm endoscope. (The 12 mm indicates the outer diameter of the endoscope.) The endoscope's design wavelengths are 486 nm, 587 nm, and 656 nm. The endoscope is not well focused in the near infrared, e.g., at 850 nm. Curve 401 is the change in focus position with object distance for a visible image. Curve 402 is the change in focus position with object distance for a non-visible image in the near infrared at 850 nm. Curve 403 is a difference between curves 401 and 402.

As shown by curve 403, the difference in focus positions is effectively a constant over the range of object distances. Thus, lens 331 for this endoscope is selected to compensate for the delta in focus represented by curve 403 so that when near infrared light from an endoscope is passed through lens 331, the focus is corrected and curves 401 and 402 are coincident for the working distances of interest.

FIG. 4B is for an 8.5 mm endoscope. Curve 411 is the change is focal position with object distance for a visible image. Curve 412 is the change in focal position with object distance for a non-visible image in the near infrared at 850 nm. Curve 413 is the difference between curve 411 and 412.

In this example, the differences in focus in FIGS. 4A and 4B are too great to correct using a common lens. Thus, two different lenses are used one for the correction needed as represented by curve 403 and another for the correction needed as represented by curve 413.

As shown by curve 413, the difference in focus position is relatively constant over the range of object distances of interest. In this example, the differences in focal position in FIGS. 4A and 4B are too great to correct using a common lens. Thus, two different lenses are used one for the correction needed as represented by curve 403 and another for the correction needed as represented by curve 413. Thus, lens 331 for this endoscope used to generate the data in FIG. 4B is selected to compensate for the delta in focus represented by curve 413 so that when a near infrared image is passed through lens 331, the focus is corrected and curves 411 and 412 are coincident for the working distances of interest.

Figure 5:
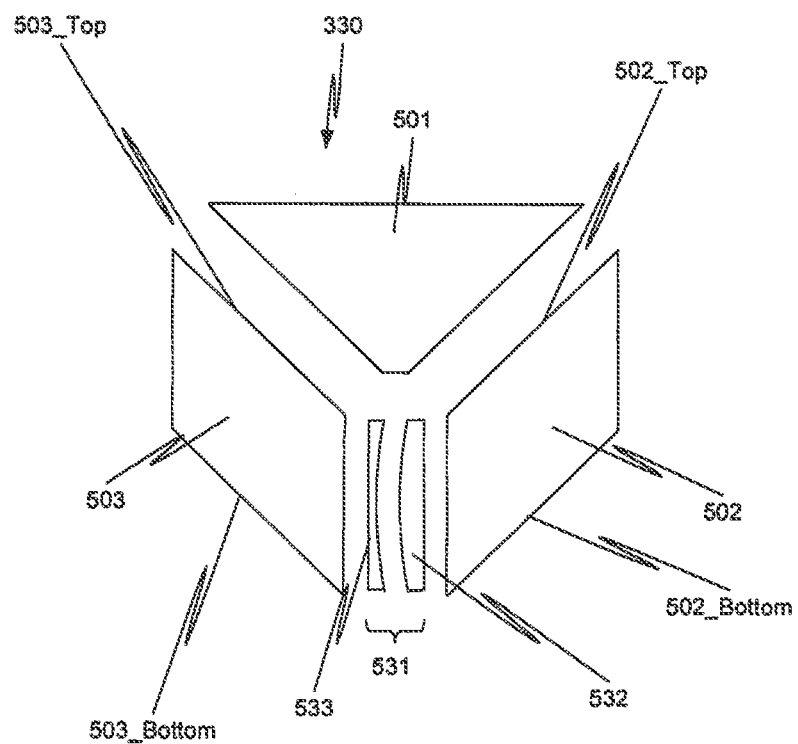
FIG. 5 is a more detailed illustration of one example of a prismatic element.

FIG. 5 is a more detailed illustration of one example of prismatic element 330. Prismatic element 330A includes a large right angle prism 501 with the top cut off as illustrated in FIG. 5. The top cut dimension is not critical. Prismatic element 330 also includes two rhomboid prisms 502, 503 and lens 531.

In this example lens 531 is a concave lens 533 of one type of glass combined with a convex lens 532 of another glass type to produce a doublet, which has a convenient thickness for manufacturing the prism assembly, and which provides the focus correction required.

As known to those knowledgeable in the field, a rhomboid prism displaces an incident beam without angular deviation or orientation changes in the image. Rhomboid prism 502 has a first coating on a first face 502_Top, and optionally a second coating on a second face 502_Bottom that is opposite and removed from first face 502_Top. Rhomboid prism 503 also has the first coating on first face 503_Top, and optionally the second coating on second face 503_Bottom.

In one aspect, when the non-visible image is in the near infrared portion of the electromagnetic radiation spectrum, the first coating is a short pass, long reflect coating with a transition near 808 nm. This means that the first coating passes wavelengths shorter than about 808 nm and reflects wavelength longer than about 808 nm. This coating, in one aspect, is on prism glass 502_Top, 503_Top and sandwiched with optical adhesive to prism 501. Thus, the coating is buried. The coating could also be placed on legs of prism 501 instead of the rhomboid prisms. The second coating only needs to reflect the non-visible image, and does not need to have any special band pass characteristics. The second coating can be implemented with a metallic mirror coating. In another aspect, it is also possible to use total internal reflection at this surface however, for manufacturability and ease of handling, a metallic mirror coating performs well.

Here, first and second are used as adjectives to distinguish between coatings and are not intended to indicate a number of coatings on a particular surface. Also, top, bottom, and side are used as adjectives to aid in distinguishing between elements as viewed in the drawings, and to help visualize relative relationships between the elements. For example, top and bottom surfaces are first and second surfaces that are opposite and removed from each other. A side surface is a third surface that extends between the first and second surfaces.

Top, bottom, and side are not being used to define absolute physical positions. In the actual implementation, endoscopic image 601 (FIG. 6A) enters the physical bottom of the camera so that prismatic element 330 is located in the physical bottom part of the camera. Thus, the part of rhomboid prism 502 in FIG. 6A through which endoscope image 601 enters is a bottom of the prism, when the prismatic element is in the camera and the camera is connected to the endoscope.

Figure 6E:
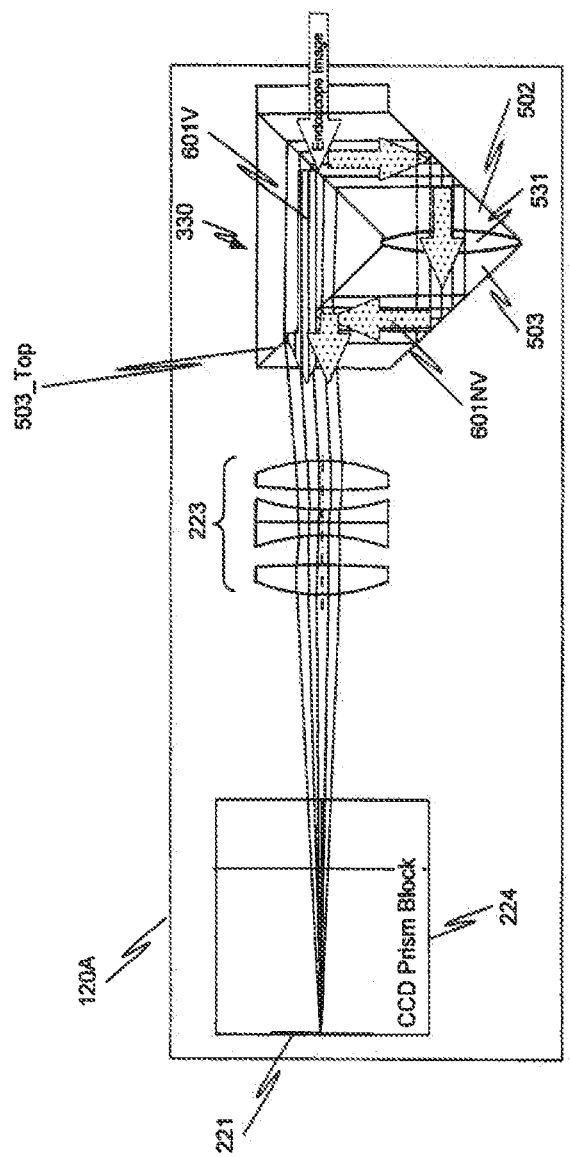

FIGS. 6A to 6E are used to explain the operation of prismatic element 330 (FIGS. 3 and 5) in camera 120A. Light from the endoscope is used to form an image, and we refer to this light as an "endoscope image" 601 (FIG. 6A). Endoscope image 601 includes a visible image formed from the visible light and a non-visible image formed from the non visible light. Endoscope image 601 first passes through a window 602. The side of rhomboid prism 502 adjacent window 602 is a square in one aspect, but the opening in the camera wall is circular. Thus, in this aspect, window 602 is a round window. In one aspect, prismatic element 330 is sixteen millimeters thick and a one millimeter thick round window is positioned with a small air gap (not shown) at the side of rhomboid prism 502. In one aspect, window 602 is a Schott BK7 glass window.

After passing through window 602, endoscopic image 601 passes through a side wall of rhomboid prism 502 to the first coating on face 502_Top of rhomboid prism 502. (FIG. 6A.) The first coating on face 502_Top, an example of a first surface, separates non-visible light 601NV (FIG. 6B) from visible light 601V. Specifically, visible light 601V is passed through the first coating. Non-visible light 601NV is reflected by the first coating on face 502_Top of rhomboid prism 502.

Reflected non-visible light 601 NV is reflected again by the second coating on face 502_Bottom, an example of a second surface. The reflected non-visible light from the second coating passes through lens 531 (FIG. 6O). Lens 531 corrects the focus of non-visible light 601I. The focus-corrected non-visible light 601NV is reflected by the second coating on face 503_Bottom of rhomboid prism 503 (FIG. 6D), an example of a third surface.

The reflected focus-corrected non-visible light 601NV from face 503_Bottom of rhomboid prism 503 (FIG. 6D) is again reflected by the first coating on face 503_Top of rhomboid prism 503 (FIG. 6E), an example of a fourth surface that is opposite and removed from the third surface. The first coating on face 503_Top of rhomboid prism 503 also passes visible light 601V through the coating. Thus, the first coating on face 503_Top of rhomboid prism 503 recombines visible light 601V and focus-corrected non-visible light 601NV. The recombined light is passed through focus lens group 223, which forms both visible and non-visible light images correctly on COD 221.

Prismatic element 330 with lens 531 fixes the mismatched visible and non-visible focus, Prismatic element 330 is substituted for the camera front window, but no other modifications to the camera or the endoscope are needed to implement the focus correction.

The above example was for non-visible light in the near infrared spectrum. However, in view of this disclosure, a prismatic element can be implemented for non-visible light in other parts of the electromagnetic radiation spectrum by selecting proper coatings. Also, in the above example, the non-visible light was focused corrected and the visible light was simply passed through the prismatic element. In some aspects, it may be advantageous to focus correct the visible light and pass through the non-visible light using a prismatic element with a lens. In still other aspects, both the visible light and the non-visible light can be passed through lenses in the prismatic element to obtain the desired focus.

The prisms described above for prismatic element 330 are illustrative only and are not intended to be limiting. In view of the above description, those of skill can implement an element that separates visible and non-visible light, focus corrects the light corresponding to one of the images and then recombines the light. For example, FIGS. 7A to 7E illustrative alternative implementations of prismatic element 330.

In FIGS. 7A to 7E, a solid line is used to represent both the light from the endoscope that contains both visible and non-visible light, and the recombined light that allows for the formation of the focus corrected image. A dashed line represents the light that is extracted from the endoscopic light and is typically focus corrected. A dashed and dotted line is used to represent the light that is passed through the prismatic element. Depending on a particular implementation, the focus-corrected light component can be either of the visible light, the non-visible light, or both. Proper coatings are selected to pass through one of the two light components and reflect the other of the two light components. Here, the light components are the non-visible light and the visible light.

Figure 7A:
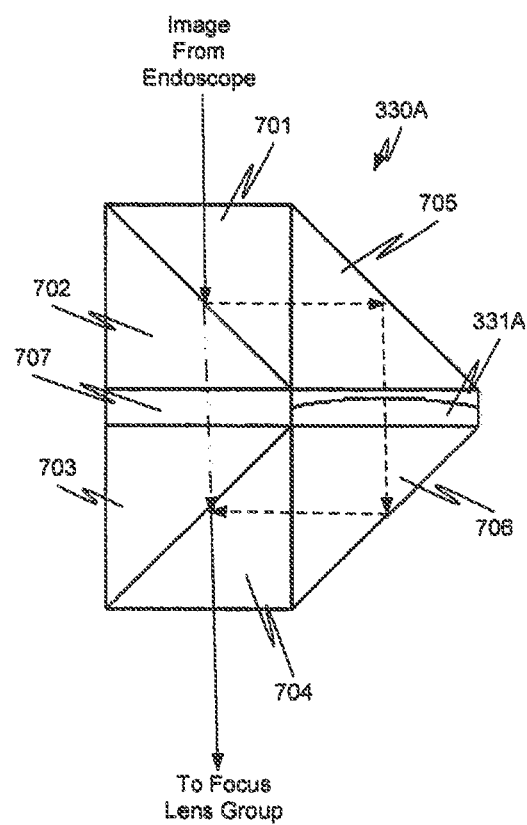
Figure 7B:
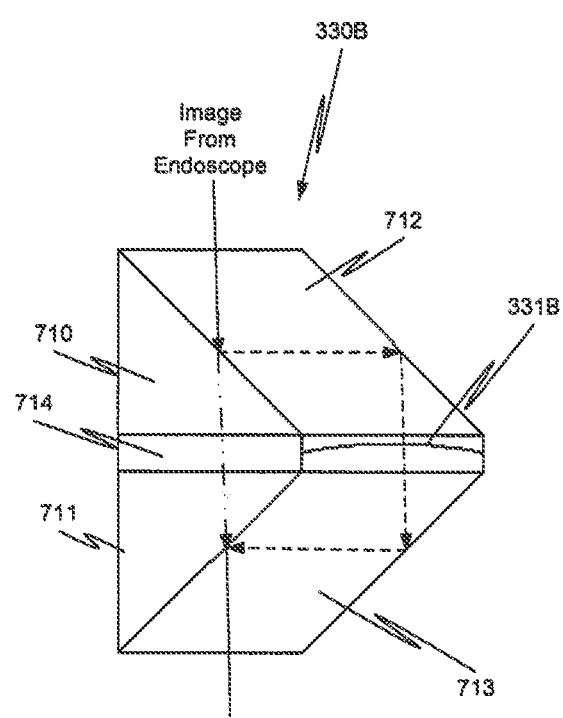

In FIG. 7A, prismatic element 330A includes six right angle prisms 701, 702, 703, 704, 705, and 706 and a lens 331A. A spacer 707 is positioned between prisms 702 and 703. Lens 331A is positioned adjacent to spacer 707 and between prisms 705 and 706. The position of spacer 707 and lens 331A can be interchanged. Also, spacer 707 could be replaced with a second lens. A pass, reflect coating, e.g., a first coating, is placed on a surface of prisms 701 and 704. A reflective coating, e.g., a second coating, is placed on a surface of prism 705 and 706.

Prismatic element 330A uses one style of prism, which is convenient for manufacturing. The pass, reflect coating could be applied on the hypotenuse of either prism 701 or prism 702 and prism 704 or prism 703 and the coating design would need to accommodate for the bonding method used to affix prism 701 to prism 702 and prism 703 to prism 704. Prismatic element 330A provides more flexibility in the choices of glass for prisms 705 and 706 relative to the rhomboid approach of FIG. 7B.

Prisms 701, 702, 703, and 704 are, in the simple case, all the same glass (although this is not required). However, prisms 705 and 706 can be made of different glasses as prisms 705 and 706 are only in the non visible path and rays through prisms 705 and 706 are of a certain wavelength group.

In FIG. 7E, prismatic element 330B includes two right angle prisms 710, 711, two rhomboid prisms 712, 713, and a lens 331B. A spacer 714 is positioned between prisms 710 and 711. Lens 331B is positioned adjacent to spacer 714 and between prisms 712 and 713. The position of spacer 714 and lens 331B can be interchanged. Also, spacer 714 could be replaced with a second lens. Rhomboid prisms 712 and 713 have coatings equivalent to those described above with respect to FIG. 5. Prismatic element 330B has fewer elements than prismatic element 330A and so there are fewer glued surfaces, which provides better alignment.

Figure 7C:
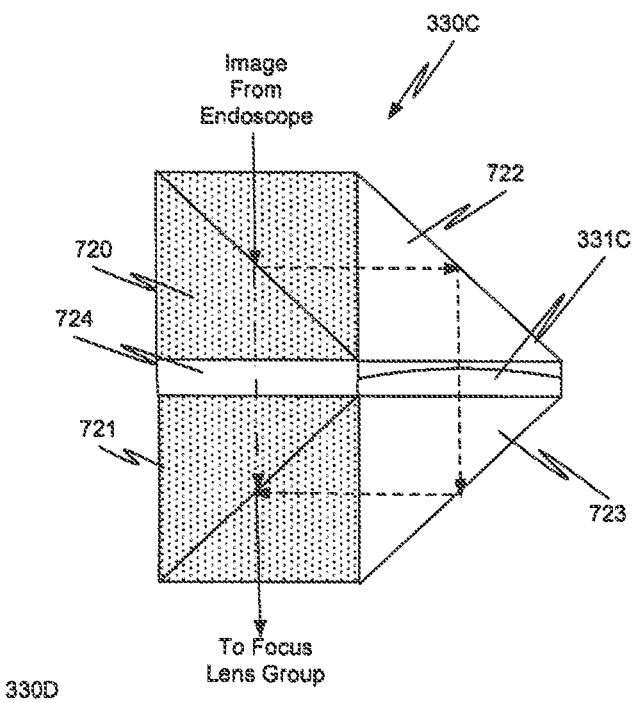

In FIG. 7C, prismatic element 330C includes two cube beam splitters 720, 721, two right angle prisms 722, 723, and a lens 331C. A spacer 724 is positioned between cube beam splitters 720, 721.
Lens 331C is positioned adjacent to spacer 724 and between prisms 722 and 723. The position of spacer 724 and lens 331C can be interchanged. Also, spacer 724 could be replaced with a second lens.

Figure 7D:
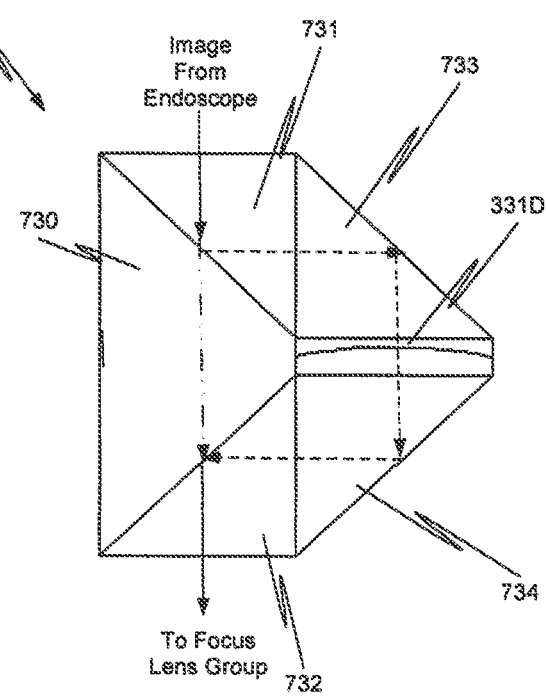

In FIG. 7D, prismatic element 330D includes one large right angle prism 730, four small right angle prisms 731, 732, 734, 735, and a lens 731D. Prism 730 has the top cut off so that lens 731D can be placed between prisms 733 and 734, Prismatic element 330D allows a glass choice on prisms 733, 734. Also, this configuration enables lens 331D to be made as part of prisms 733, 734 if desired, see below.

In FIG. 7E, prismatic element 330E includes one large right angle prism 740, two small right angle prisms 741, 742 and two prisms 743, 744 that each have a face configured to form lens 331E. Alternatively, prisms 741, 743 could be implemented as a rhomboid prism with a face configured as shown in FIG. 7E. Prisms 743 and 744 are of different glasses. Prisms 743 and 744 could also have a radius on their hypotenuse.

The above description and the accompanying drawings that illustrate aspects and embodiments of the present inventions should not be taken as limiting. For example, prismatic element 330, which is an example of a prism assembly, and focus lens group 223 could be in reverse order in the light path. Also, prismatic element 333 could be located in a separate component positioned between the camera and the endoscope. Further, prismatic element 330 could be located in the endoscope just before the exit window to the camera.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms— such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

In view of this disclosure, instructions used in any one of, or any combination of operations described with respect to the augmented display system can be implemented in a wide variety of computer system configurations using an operating system and computer programming language of interest to the user.

All examples and illustrative references are non-limiting and should not be used to limit the claims to specific implementations and embodiments described herein and their equivalents. The headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

I claim:

1. A minimally invasive surgical system comprising:
a camera including a prismatic element; and
a lens,
wherein the prismatic element passes one of a visible light spectrum and a non-visible light spectrum though a straight optical path,
wherein the prismatic element passes an other of the visible light spectrum and the non-visible light spectrum through a folded optical path, and
wherein the lens corrects a focus of an image formed from the one of the visible light spectrum and the non-visible light spectrum so that the focus of the image is about the same as a focus of another image formed from the other of the visible light spectrum and non-visible light spectrum that passes through the prismatic element.

2. The minimally invasive surgical system of claim 1, wherein the folded optical path comprises the lens.

3. The minimally invasive surgical system of claim 1, wherein the lens is within the prismatic element.

4. The minimally invasive surgical system of claim 3, wherein the lens is formed in a face of a prism within the prismatic element.

5. The minimally invasive surgical system of claim 3,
wherein the prismatic element comprises a plurality of prisms, and
wherein the lens is formed in faces of two adjacent prisms in the plurality of prisms.

6. The minimally invasive surgical system of claim 3, wherein the lens is changeably insertable into the prismatic element.

7. The minimally invasive surgical system of claim 1, wherein only one of the straight optical path and the folded optical path includes the lens.

8. The minimally invasive surgical system of claim 1, wherein the folded optical path and the straight optical path both extend between a common start location and a common end location.

9. The minimally invasive surgical system of claim 8, further comprising:
a focus lens group; and
an imaging sensor,
wherein the visible light spectrum and the non-visible light spectrum are combined into combined light at the common end location, and
wherein the focus lens group focuses the combined light onto the imaging sensor.

10. The minimally invasive surgical system of claim 9, wherein the focus lens group focuses the combined light into a visible light spectrum image and a non-visible light spectrum image on the imaging sensor.

11. The minimallyy invasive surgical system of claim 1, wherein the prismatic element comprises a first surface having a pass, reflect coating, wherein the coating passes the one of the visible light spectrum and the non-visible light spectrum through the coating, and reflects the other of the visible light spectrum and non-visible light spectrum.

12. The minimally invasive surgical system of claim 11, wherein the prismatic element further comprises a second surface, opposite and removed from the first surface, having a reflect coating.

13. The minimally invasive surgical system of claim 12, wherein the prismatic element further comprises a third surface, different from the first surface, having the bass, reflect coating.

14. The minimally invasive surgical system of claim 1, wherein the prismatic element includes a plurality of prisms.

15. The minimally invasive surgical system of claim 1, wherein the non-visible light spectrum is included in fluorescence.

16. The minimally invasive surgical system of claim 15, wherein the fluorescence comprises light in the near infrared spectrum.

17. The minimally invasive surgical system of claim 1, wherein the non-visible light spectrum is a narrow band spectrum that corresponds to a fluorescence emission spectrum of a medical fluorophore.

18. The minimally invasive surgical system of claim 1, wherein the prismatic element passes the non-visible light spectrum through the folded optical path.

\* \* \* \* \*